United States Patent [19]

Hirota et al.

[11] Patent Number: 5,747,671
[45] Date of Patent: May 5, 1998

[54] AXIAL FLOW PARTICLE SENSOR

[75] Inventors: Toshikazu Hirota; Kazuyoshi Shibata, both of Nagoya; Yukihisa Takeuchi, Nishikamo-gun, all of Japan

[73] Assignee: NGK Insulators, Ltd., Japan

[21] Appl. No.: 726,172

[22] Filed: Oct. 4, 1996

[30] Foreign Application Priority Data

Oct. 20, 1995 [JP] Japan .................. 7-272205

[51] Int. Cl.⁶ .................................. H01L 41/08
[52] U.S. Cl. ............. 73/61.75; 73/861.21; 73/861.73; 310/338
[58] Field of Search ............... 73/61.75, 861.04, 73/861.18, 861.21, 861.73, 19.03, 24.01, 24.03, 54.41, 61.45, 61.49, 61.79; 310/311, 323, 324, 325, 328, 338, 358

[56] References Cited

U.S. PATENT DOCUMENTS

| | | | |
|---|---|---|---|
| 3,557,616 | 1/1971 | Landon, Jr. et al. | 73/861.73 |
| 3,561,153 | 2/1971 | Dorman | 310/338 X |
| 3,653,253 | 4/1972 | Olin | 73/61.75 X |
| 3,715,911 | 2/1973 | Chuan | 73/24.03 |
| 3,805,591 | 4/1974 | Willis et al. | 73/24.03 |
| 3,816,773 | 6/1974 | Baldwin et al. | 73/61.75 X |
| 3,841,144 | 10/1974 | Baldwin | 73/61.75 |
| 3,857,049 | 12/1974 | Zoltan | 310/328 |
| 4,240,287 | 12/1980 | Mast et al. | 73/61.75 |
| 4,432,228 | 2/1984 | Kuschmierz et al. | 310/338 X |
| 4,872,335 | 10/1989 | Tsuruoka et al. | 73/24.01 |
| 5,201,322 | 4/1993 | Henry et al. | 73/861.21 X |
| 5,455,475 | 10/1995 | Josse et al. | 310/338 X |
| 5,616,872 | 4/1997 | O'Brien | 73/61.75 X |

FOREIGN PATENT DOCUMENTS

| | | |
|---|---|---|
| 57-79800 | 5/1982 | Japan ............. 310/324 |
| 3-128680 | 5/1991 | Japan . |
| 3-128681 | 5/1991 | Japan . |
| 4-12678 | 1/1992 | Japan . |
| 7-301594 | 11/1995 | Japan . |
| 2249176 | 4/1992 | United Kingdom . |
| WO 93/09405 | 5/1993 | WIPO . |

Primary Examiner—George M. Dombroske
Assistant Examiner—Paul D. Amrozowicz
Attorney, Agent, or Firm—Parkhurst & Wendel

[57] ABSTRACT

An axial-flow particle sensor has a sensor element and a housing. The outlet of fluid is placed at the opposite side of the inlet of the fluid, throughholes are formed at the circumference of the vibrating portion of the sensor element, and the vibrating portion of the sensor element is placed on the extension of the flow of the fluid so that the fluid entering from the inlet flows through the throughholes and flows out from the outlet. Two or more throughholes may be formed symmetrically with the axis. The throughhole may be formed on a ceramic substrate, or may be a gap between the ceramic substrate and the housing.

11 Claims, 8 Drawing Sheets

AXIAL FLOW PARTICLE SENSOR

BACKGROUND OF THE INVENTION

The present invention relates to a particle sensor for detecting solid particles in a fluid.

When a fluid, such as a liquid or a gas, contains solid particles, it is sometimes necessary to detect the presence of the particles. Particularly, when the particles are undesirably present in a fluid and impede the function of the fluid, the detection of such particles becomes important.

For example, internal combustion engines such as engines for motor vehicles or heavy-duty machines use gasoline or gas oil as their power source. These internal combustion engines use a lubricant to reduce friction resistance and abrasion on rotating or sliding surfaces of the engines and the like. In such internal combustion engines, however, particles such as metal powder produced by abrasion may mix in the lubricant and accelerate the abrasion of the rotating or sliding surfaces. Although particles in the lubricant are generally removed by a filter such as an oil filter, lubricant conditions can be monitored in more detail by detecting metal particles in the lubricant.

It is important to control the conditions of fluids by controlling particles therein and/or the viscosity of the fluids such as machine oil and cleaning oil used not only for internal combustion engines such as engines, but also for power transmission mechanisms such as transmission gears, piping systems such as hydraulic servo systems, and industrial rolling and pressing.

The presence of floating particles in the air and their concentration are important factors for monitoring air pollution. For example, it is important to detect floating particles in smoke exhausted from factories. Note that fluid is the general term for gas and liquid, and these media are not necessarily moving.

Japanese Patent Application No. 6-304579 (1994) discloses a particle sensor utilizing a piezoelectric film. When a particle in a fluid collides with a detector having a piezoelectric film, or a vibrating portion carrying the detector, the detector and the vibrator vibrate, the piezoelectric film converts this vibration to electric signals, and electrodes on both ends of the piezoelectric film output these electric signals.

However, since the detector disclosed in Japanese Patent Application No. 6-304579 has no means for controlling the flow rate of a fluid, sensitivity to fine particles is low. Also, if the position of the detector is dislocated, the flow of the fluid may become difficult to collide with the detector or the vibrator.

International Patent Application Laid-Open No. WO93/09405 discloses a sand detector comprising a probe extending almost perpendicularly to the fluid flow, and a sensor for detecting the vibration of the probe at the foot of probe. GB 2,249,176A discloses a particle sensor using an ultrasonic transducer and a probe.

In either International Patent Application Laid-Open WO93/09405 or GB 2,249,176A, however, since the area of the probe is much smaller than the cross-sectional area of fluid flow, the probability of collision of particles in the fluid with the probe is low, and since the detector has no means for controlling the flow rate of a fluid, sensitivity to fine particles is low. Especially, the problem arises when the amount of flowing fluid is small.

It is the object of the present invention to solve the above-mentioned problems, and to let the flow of a fluid collide with the vibrating portion or the detector by regulating the fluid flow in the vicinity of the sensor element, preferably by positioning the sensor element itself at the center of fluid flow.

SUMMARY OF THE INVENTION

According to the present invention, an axial-flow particle sensor comprising a sensor element comprising a vibrating portion having a sufficient mass for responding to the collision of a solid particle in a fluid and a converter for detecting the vibration of said vibrating portion and converting the vibration to electric signals; a housing for fixing said sensor element; an inlet of fluid; and an outlet of fluid; wherein said outlet is located in the opposite side of said inlet relative to said sensor element, a throughhole is opened in at least a part of the circumference of said vibrating portion, and said vibrating portion of said sensor element is located at the extension of fluid flow formed at said inlet so that the fluid entering from said inlet flows through said throughhole and flows out from said outlet, is provided.

In the present invention, it is preferred that said inlet is placed coaxially with said outlet, and said vibrating portion of said sensor element is placed coaxially with said inlet and said outlet.

Furthermore, it is preferred that said vibrating portion has a plate-like form, and the extending direction of the plate of said vibrating portion is almost perpendicular to the direction of fluid flow formed at said inlet.

Also, it is preferred that two or more throughholes are formed symmetrically with said axis.

Furthermore, said sensor element may have a ceramic substrate, said vibrating portion may be a part of said ceramic substrate, and said throughhole may be formed on said ceramic substrate. Alternatively, said sensor element may have a ceramic substrate, said vibrating portion may be a part of said ceramic substrate, and said throughhole may be a gap between said ceramic substrate and said housing.

Furthermore, said converter may be placed on said inlet side relative to said vibrating portion. Alternatively, said converter may be placed on said outlet side relative to said vibrating portion.

Also, it is preferred that the sectional area of said inlet is smaller than the sectional area of said outlet.

It is further preferred that said converter is one selected from the group consisting of: that utilizing piezoelectricity, that utilizing electromagnetic induction, that utilizing change in static capacitance, that emitting light on to said vibration portion and utilizing change in incident light at the light receiving portion, that utilizing change in electric resistance due to the strain of the conductor, and that utilizing change in electric resistance due to the strain of the semiconductor, or a combination thereof.

It is further preferred that said sensor element comprises a detecting portion having a piezoelectric film consisting of a ceramic material, a first electrode covering at least a part of the outer surface of said piezoelectric film, and a second electrode covering at least a part of the inner surface of said piezoelectric film; a vibrating portion carrying said detecting portion and consisting of a ceramic material; and a fixing portion for fixing said vibrating portion so as to allow said vibrating portion to vibrate.

PREFERRED EMBODIMENTS OF THE INVENTION

Figure 1:
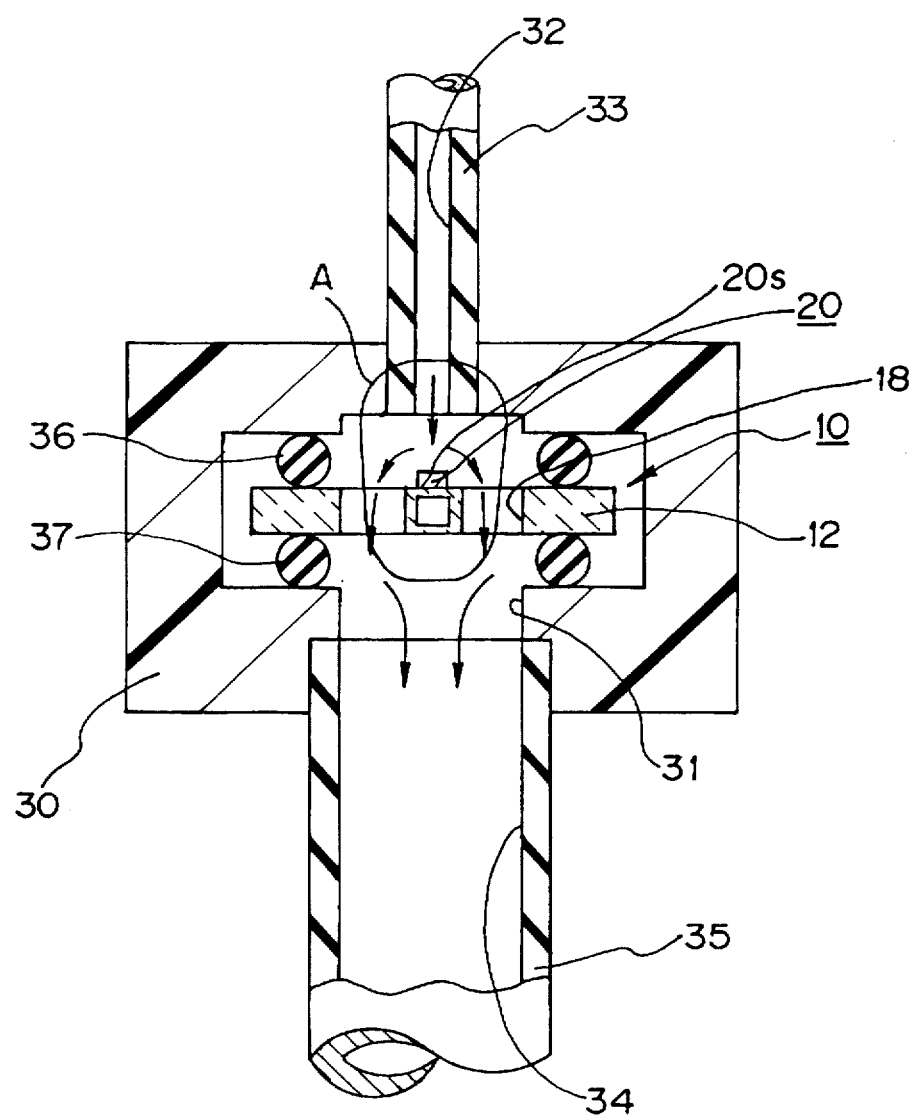
FIG. 1 is a cross-sectional view of an axial-flow particle sensor of the present invention.

In FIGS. 1, 2, 3A and 3B, the sensor element 10 has a substrate 12, and a detecting portion 20 fixed on the vibrating portion 14 of the substrate 12. The detecting portion 20 detects vibrations of the vibrating portion 14, and converts them into electric signals.

The substrate 12 is plate-like as a whole, and a pair of throughholes 18 are opened through the substrate 12 in the thickness direction. Although the number and shape of the throughholes are not limited, it is preferred that the pair of throughholes 18 are of a shape identical to each other, and are arranged symmetrically relative to a virtual plane passing through the vibrating portion 14 in the axial direction.

The sensor element 10 is fixed inside a housing 30 via elastic members 36 and 37, such as O-rings. In the present invention, the means for fixing the sensor element on to the housing is not limited, and screws or adhesives may be used.

The flow of the fluid is controlled by the elastic members 36 and 37 so that the fluid flows inside the elastic members 36 and 37. However, the flow of the fluid may be controlled by the internal configuration of the housing, or a means for connecting the substrate and the housing.

To the housing 30 is fixed a nozzle 33 which allows the fluid to flow into the housing 30, and forms the inlet 32 of the fluid. In FIG. 1, the nozzle 33 passes through the wall portion of the housing 30. Also fixed to the housing 30 is another nozzle 35 which allows the fluid to flow out of the housing 30, and forms the outlet 34 of the fluid. The housing 30 has an opening 31, and the nozzle 35 is fixed to the opening 31.

It is preferred that the nozzles 33 and 35 are located coaxially, and that the inlet 32 and the outlet 34 are also located coaxially. The sectional area of the nozzle 33 is preferably smaller than the sectional area of the nozzle 35. That is, the sectional area of the inlet 32 is smaller than the sectional area of the outlet 34. According to such a structure the flow rate of the fluid at the inlet 32 is made faster than the flow rate of the fluid at the outlet 34. This is preferred because when the flow rate at the inlet 32 is faster, the impact of particles in the fluid to the detecting portion 20 or the vibrating portion 14 increases, thus improving the sensitivity to fine particles having a particle diameter of 10μm or less.

The outlet 34 is fixed at the location opposite to the inlet 32 relative to the substrate 12 of the sensor element 10. The fluid flows into the housing 30 through the inlet 32, is interfered with by the vibrating portion 14 and the detecting portion 20, flows through the holes 18, and flows out of the outlet 34.

According to the present invention, the vibrating portion 14 of the sensor element 10 is located on the extension of the flow of the fluid 42 formed at the inlet 32, so that the fluid flowing through the inlet 32 flows through the throughholes 18 and flows out of the outlet 34. By this the probability that the flow of the fluid and solid particles in the fluid collide with the vibrating portion 14 or the detecting portion 20 increases. For example, when the nozzle 33 is linear without bending as FIG. 1 shows, since the fluid flows straight in the nozzle 33, it is preferred that the vibrating portion 14 and the detecting portion 20 of the sensor element 10 are located in the region of the boundary 47 which is the extension of the inner diameter 33s of the nozzle 33 in the axial direction. However, even if the vibrating portion 14 and the detecting portion 20 of the sensor element 10 are located out of the boundary 47 which is the extension of the inner diameter 33s of the nozzle 33 in the axial direction, since the flow of the fluid expands in the direction perpendicular to the axis from the inlet 32 as the fluid flows into the housing 30, these may be located on the extension of this expanded flow of the liquid.

It is not necessary that the vibration portion 14 and the detecting portion 20 are located symmetrically relative to the center line 46. According to the present invention, even if the vibrating portion 14 and the detecting portion 20 are deviated from the center line 46, the vibrating portion 14 and the detecting portion 20 are located at the center of the flow in the flow of the fluid from the inlet 32 to the throughholes 18, that is, in the vicinity of the vibrating portion 14 and the detecting portion 20. However, it is preferred that the vibrating portion 14 and the detecting portion 20 are located symmetrically relative to the center line 46.

Although the surface 14s of the vibrating portion 14 and the surface 20s of the detecting portion 20 face to the inlet 32, the area of the surface 14s of the vibrating portion 14 or the area of the surface 20s of the detecting portion 20 is preferably 300% or less, more preferably 200% or less, and furthermore preferably 50% or less of the sectional area of the inlet 32, that is, the sectional area of the nozzle 33 at the inner diameter 33s. This is because in these areas, the probability that the flow of the fluid, and solid particles in the fluid collide with the vibrating portion 14 or the detecting portion 20 is high.

The inner diameter D of the inlet 32 is preferably 0.2 to 10 mm. If the inner diameter D is smaller than 0.2 mm, the flow volume may be too low, and the inlet may be choked by particles. While if the inner diameter D is larger than 10 mm, the flow rate may be too low.

Figure 2:
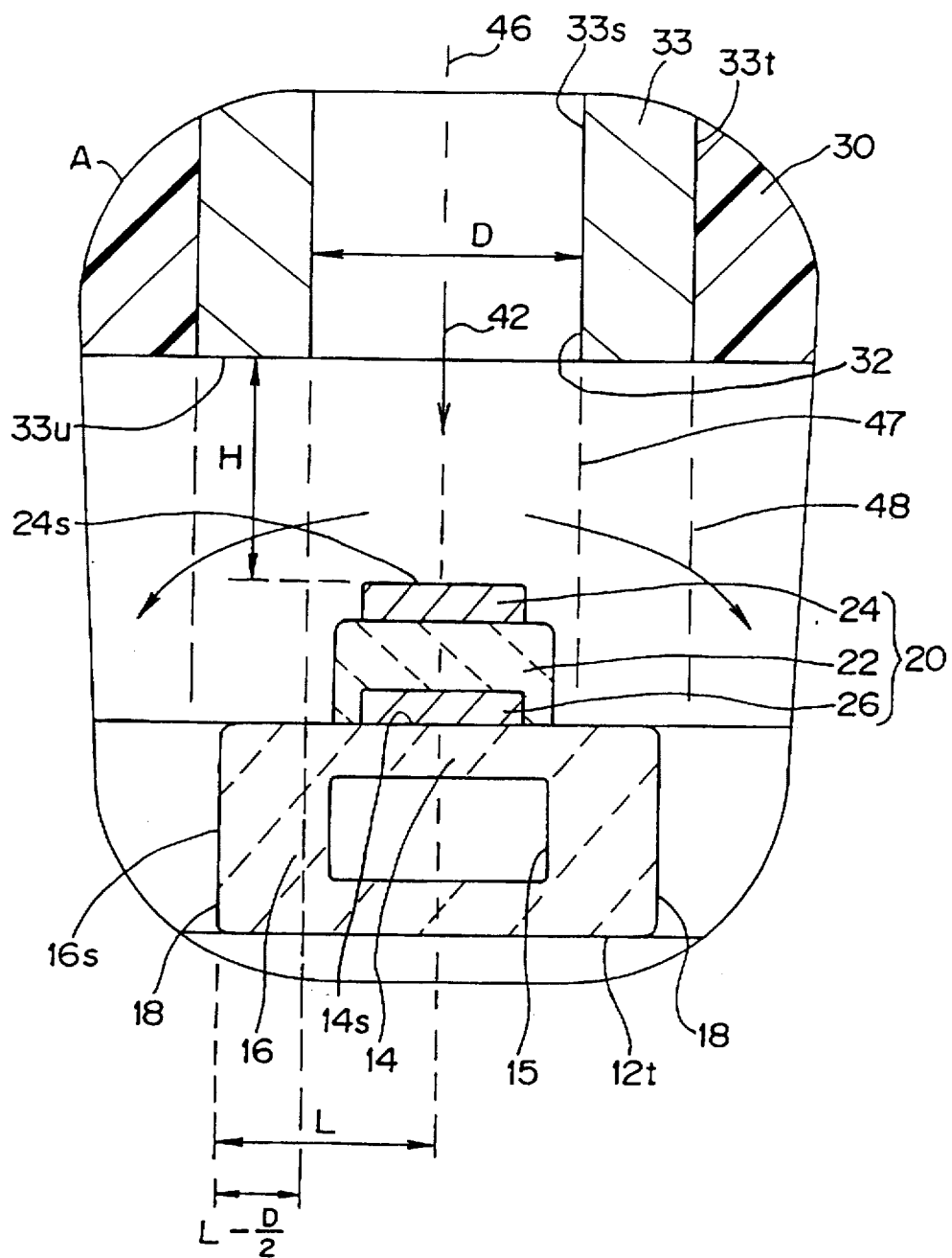
FIG. 2 is an enlarged cross-sectional view of the part A of FIG. 1.
Figure 3A:
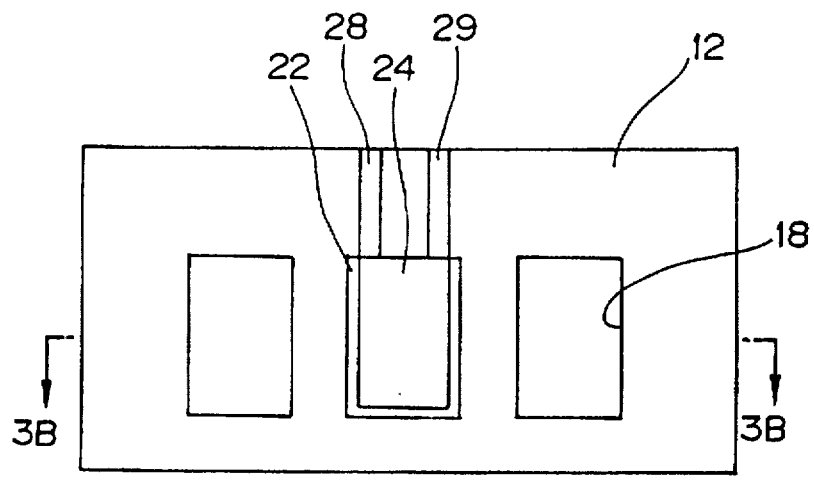
FIGS. 3A and 3B are an illustrative diagrams of a sensor element which can be used in the axial-flow particle sensor of the present invention, FIG. 3A being a front view thereof, and FIG. 3B being a cross-sectional view along the line 3B–3B'.
Figure 3B:
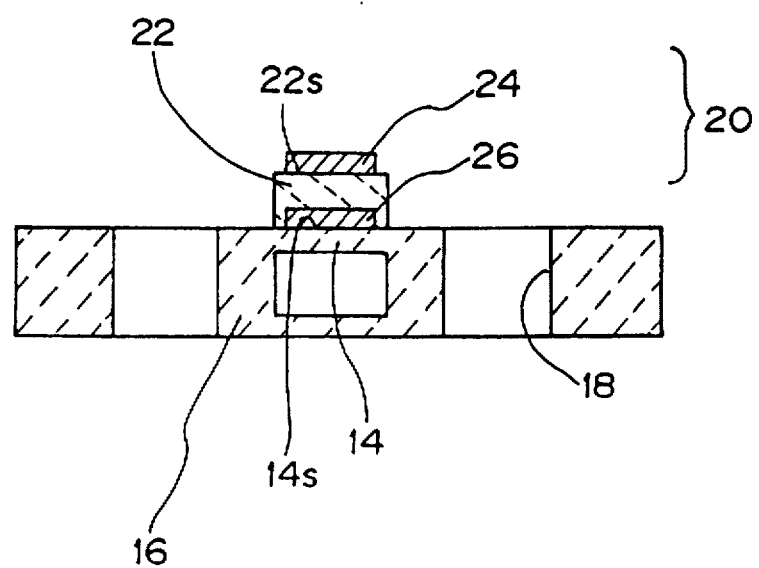
Figure 4:
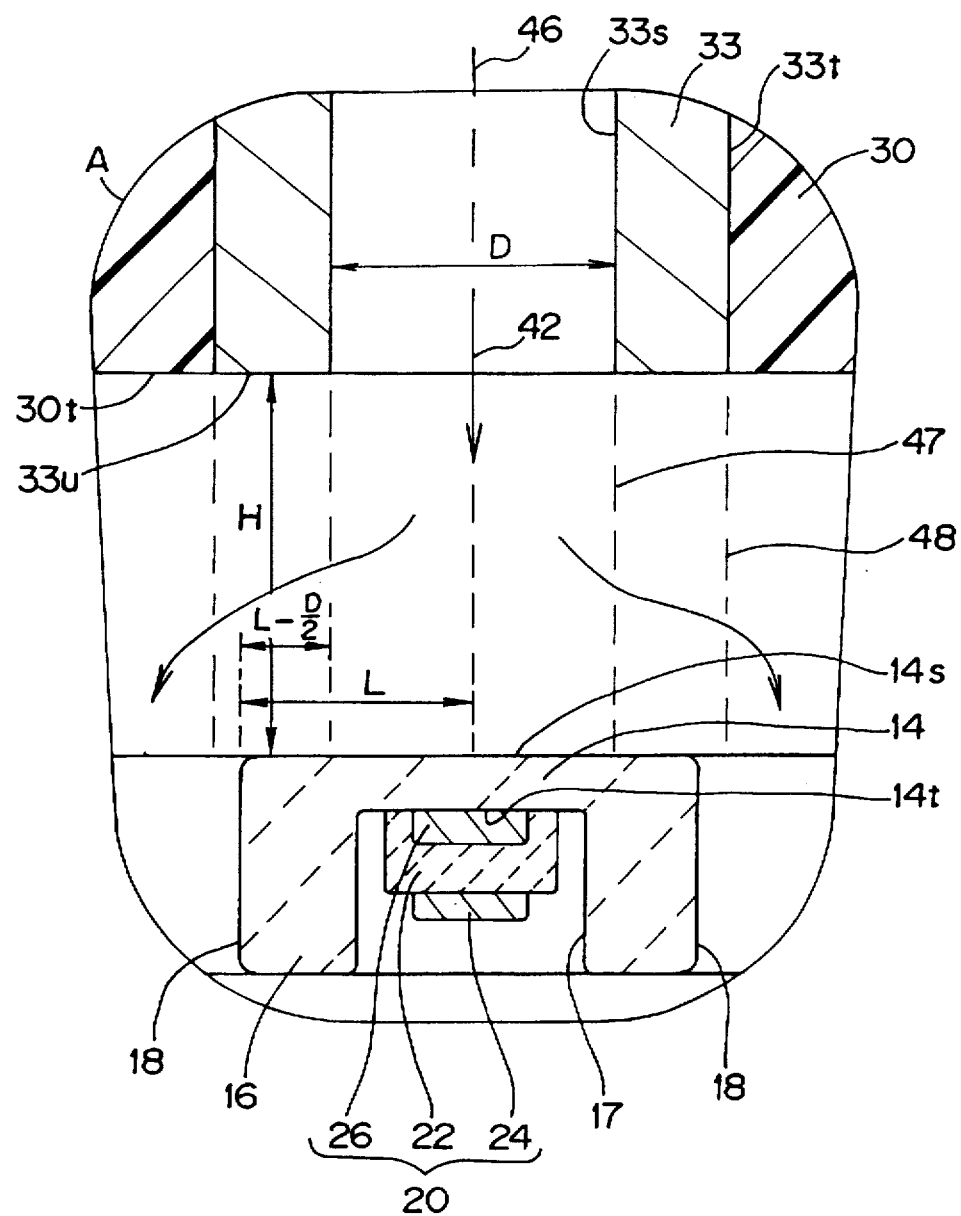
FIG. 4 shows an embodiment of the axial-flow particle sensor according to the present invention, and is a partially enlarged view corresponding to part A of FIG. 1.
Figure 5:
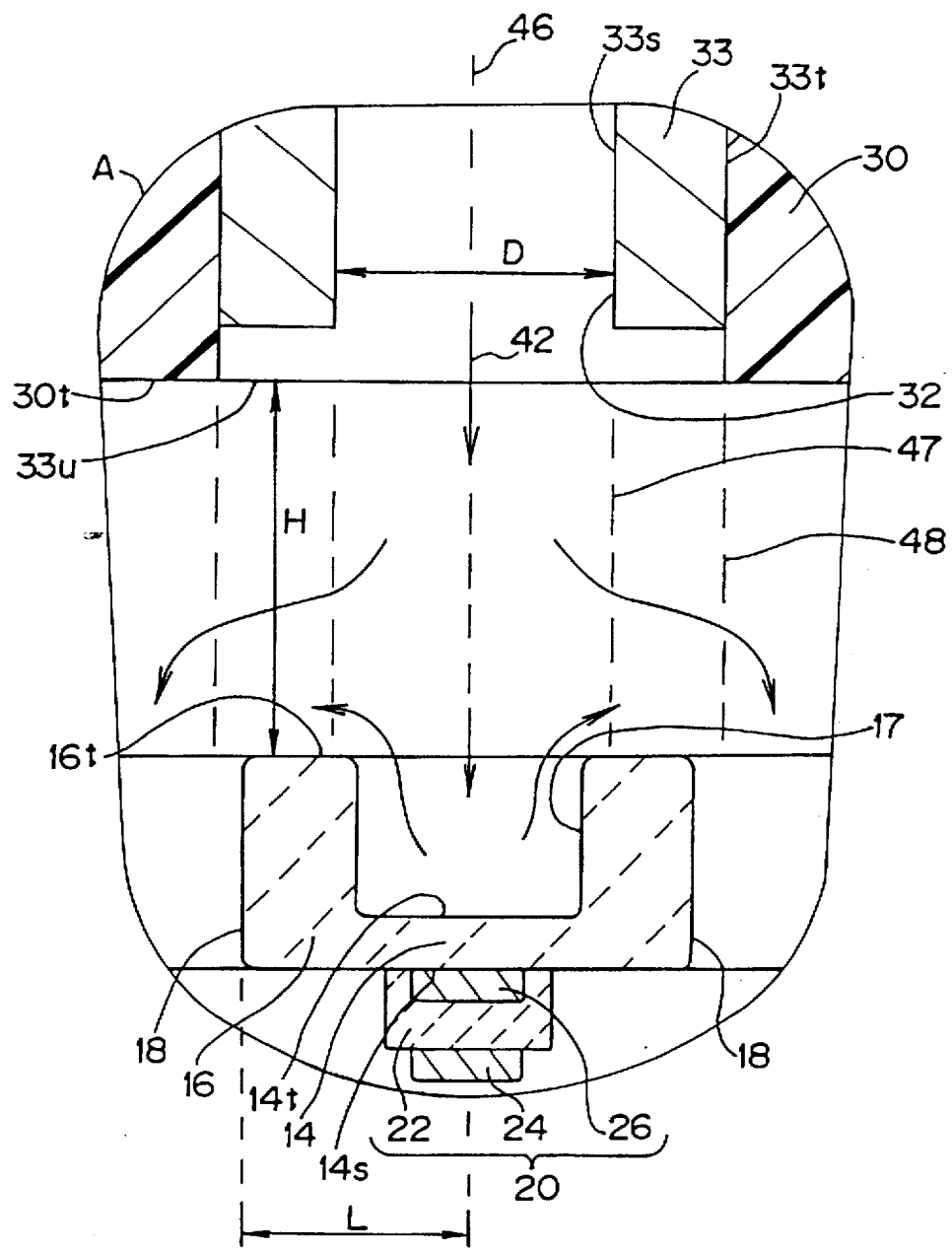
FIG. 5 shows an embodiment of the axial-flow particle sensor according to the present invention, and is a partially enlarged view corresponding to the part A of FIG. 1.
Figure 6:
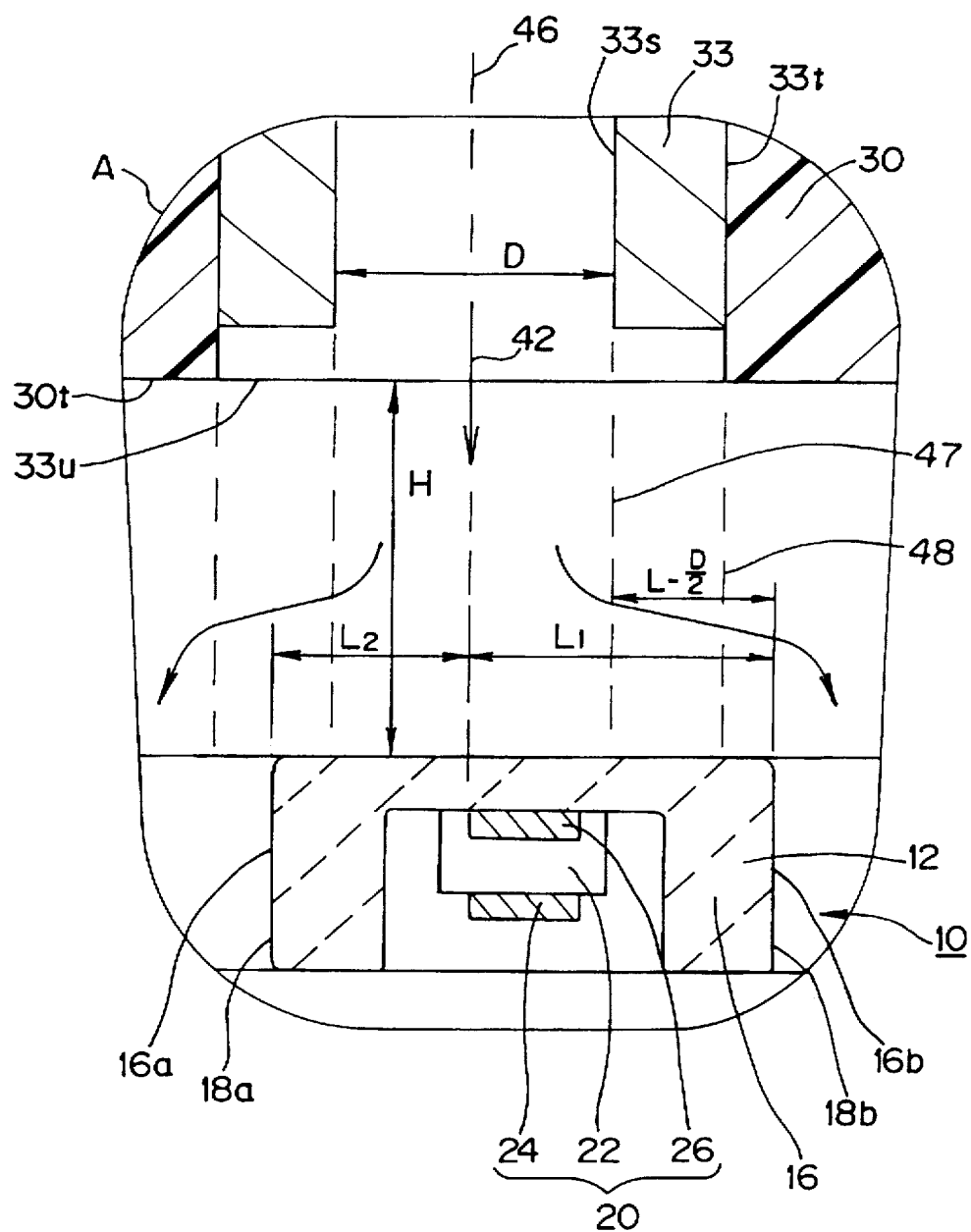
FIG. 6 shows an embodiment of the axial-flow particle sensor according to the present invention, and is a partially enlarged view corresponding to part A of FIG. 1.

The distance H between the inlet 32 and the sensor element 10 parallel to the center of the flow of the fluid is preferably 0.05 mm or more and 25 D or less, more preferably 0.1 mm or more and 10 D or less, and further preferably 0.2 mm or more and 5 D or less. Here, as FIG. 2 shows, when the detecting portion 20 is located on the inlet 32 side, and when the end surface 33u of the nozzle 33 is parallel to the surface 24s of the first electrode 24, the distance H corresponds to the distance between the end surface 33u and the surface 24s. In FIG. 4, the distance H corresponds to the distance between the end surface 33u of the nozzle 33 and the surface 14s of the vibrating portion 14. In FIG. 5, the distance H corresponds to the distance between the surface 30t of the housing 30 and the surface 16t of the fixing portion 16. If the distance H is smaller than 0.05 mm, the flow of the fluid may become stagnant between inlet 32 and sensor element 10, and noise may occur at places where flow concentrates due to cavitation. Also, the nozzle 33 may contact with and break the sensor element 10 due to design error and the like. On the other hand, if the distance H is larger than 25 D, the flow rate decreases, and sufficient impact cannot be obtained when particles collide with the sensor element. (L-D/2) is preferably 10 H or less, and more preferably 5 H or less. Here, L is the maximum distance from the central axis 46 of the nozzle 33 to the end of the throughhole 18 nearest to the central axis. In FIG. 2, for example, L is the distance from the central axis of the nozzle 33 to the surface 16s of the fixing portion 16. Here, the surface 16s of the fixing portion 16 forms throughholes 18 together with respect to other surfaces. In FIG. 6, the sensor element 10 is not located symmetrically with the central axis 46 of the nozzle 33. Surfaces 16a and 16b of the fixing portion 16 are ends of the throughholes 18a and 18b, respectively, and correspond to the nearest ones to the central axis. Since $L_1$ is larger than $L_2$, $L_1$ corresponds to L described above. In FIG. 7, L is the distance from the central axis of the nozzle 33 to the surface 16s of the fixing portion 16 for forming the gap 19.

If the area of the detecting portion 20 is larger than the inner diameter D of the inlet 32 (for example, if the area of the surface 20s of the detecting portion 20 is 100% of the sectional area of the inlet 32 or larger, in particular 200% or larger), the flow of the fluid may become stagnant at the inlet 32 when the distance H between the inlet 32 and the sensor element 10 is small. However, when the condition that (L-D/2) is 1 OH or less is satisfied, the fluid can flow smoothly at the inlet 32 even in such a case.

In the embodiments of FIGS. 1, 2 and 3, both the substrate 12 and the vibrating portion 14 are plate-like, and expand in the direction almost perpendicular to the direction of the flow of the fluid at the inlet 32. By this the vibrating portion 14 easily collides with the flow of the fluid. According to the present invention, however, the direction of expansion of the vibrating portion 14 is not required to be perpendicular to the direction of the flow of the fluid at the inlet 32.

The sensor element 10 will be described in more detail below. In the embodiments of FIGS. 2 and 3, the sensor element 10 has a substrate 12, and a detecting portion 20 placed on the vibrating portion 14 of the substrate 12.

The substrate 12 has a vibrating portion 14 and a fixing portion 16 integrated with each other, and the vibrating portion 14 and the fixing portion 16 constitute a part of the substrate 12. On the top of the vibrating portion 14 is placed a detecting portion 20, while on the bottom of the vibrating portion 14 is located the fixing portion 16 as surrounding the circumference of the vibrating portion 14.

According to the present invention, however, the vibrating portion and the fixing portion are not required to constitute part of the substrate, but for example, a fixing portion made of a metal may fix a separate vibrating portion made of a ceramic material. When the fixing portion is made of a metal, the surface of the vibrating portion to be connected to the fixing portion is metallized, which is in turn brazed to the fixing portion. Alternatively, the vibrating portion may be fixed simply by the pressure of the metal. The fixing portion may be made of a metal such as stainless steel and iron.

According to the present invention, as FIG. 1 shows, the full circumference of the vibrating portion is not required to be held by the fixing portion, but a part of the circumference of the vibrating portion may held in a so-called cantilever condition. In the embodiments of FIGS. 2 and 3, a closed space 15 is formed in the substrate 12 so that the vibrating portion 14 becomes thin, and the detecting portion 20 is provided on the surface 14s of the vibrating portion 14 on the opposite side of the closed space 15, corresponding to the location of the closed space 15.

According to the present invention, however, the space for forming the thin vibrating portion is not limited to the closed space, but the space may be a concave portion formed from the surface 12t of the substrate 12 toward the vibrating portion 14.

When the sensor element 10 detects a particle, the vibrating portion 14, together with the detecting portion 20, vibrates vertically, that is, in the direction to the detecting portion 20 and the closed space 15. For optimal vibration, the vibrating portion 14 is preferably plate-like, and in this case, the thickness of the plate is preferably 1 to 100 µm, more preferably 3 to 50 µm, and further preferably 5 to 20 µm. If the plate is thicker than 100 µm, sensitivity will decrease, and if the plate is thinner than 1 µm, the mechanical strength will decrease.

The vibrating portion 14 is preferably made of a highly heat resistant material. By this the detecting portion 20 can be placed directly on the surface of the vibrating portion 14 without using less heat resistant materials such as organic adhesives. When the sensor element is used in a lubricant such as oil, since the sensor element may contact with an organic solvent contained in the lubricant, or the lubricant may change to have acidic or alkaline properties, the vibrating portion is preferably made of a chemically stable material.

Since the second electrode which covers at least a part of the vibrating portion 14, leads 28 and 29 connected to the first and second electrodes, and lead terminals are electrically conductive, the vibrating portion 14 is preferably made of an electrically insulating material. Therefore, although the vibrating portion 14 may be made of a highly heat resistant metal coated with a ceramic material such as glass, it is preferred that the vibrating portion 14 consists of a ceramic material. Ceramic materials constituting the vibrating portion include for example, stabilized zirconium oxide, aluminum oxide, magnesium oxide, mullite, aluminum nitride, silicon nitride, and glass. Stabilized zirconium oxide is preferred because of a high mechanical strength even if the vibrating portion is thin, a high rigidity, and a low chemical reactivity with the piezoelectric film and the electrodes.

Stabilized zirconium oxide used here includes both fully stabilized zirconium oxide and partially stabilized zirconium oxide. Since stabilized zirconium oxide has a crystal structure such as cubic, it does not undergo phase transition. On the other hand, ordinary zirconium oxide undergoes phase transition at a temperature of apx. 1000° C. between monoclinic and tetragonal, and cracks are produced at this phase transition. Stabilized zirconium oxide contains 1 to 30 mol percent of a stabilizer such as calcium oxide, magnesium oxide, yttrium oxide, scandium oxide, ytterbium oxide, cerium oxide, or oxides of rare earth metals. In order to increase the mechanical strength of the vibrating portion, it is preferred that the stabilizer contains yttrium oxide. In this case, the content of yttrium oxide is preferably 1.5 to 6 mol percent, and more preferably 2 to 4 mol percent. Principal crystal phase may be tetragonal, the mixed phase of tetragonal and cubic, the mixed phase of cubic and monoclinic, mixed phase of tetragonal and monoclinic, or the mixed phase of cubic, tetragonal, and monoclinic. Of these, it is preferred that the principal crystal phase is tetragonal, or the mixed phase of tetragonal and cubic from the point of view of mechanical strength, rigidity, and durability.

The ceramic material constituting the vibrating portion 14 contains preferably 0.5 to 5 percent, more preferably 1 to 3 percent by weight of silicon oxide. This is because when the detecting portion 20 is formed by heat treatment, silicon oxide inhibits the excessive reaction between the vibrating portion 14 and the detecting portion 20.

When the vibrating portion 14 is made of a ceramic material, a large number of grains constitute the vibrating portion. In this case, in order to increase the mechanical strength of the vibrating portion, the average grain diameter of the grains is preferably 0.05 to 2 μm, and more preferably 0.1 to 1 μm.

The fixing portion 16 fixes at least a part of the vibrating portion 14, or at least a part of the circumference of the vibrating portion 14 to allow the vibrating portion 14 to vibrate. In the embodiment of FIG. 1, it is preferred that the fixing portion 16 consists of a ceramic material, and the ceramic material may be the same as the material of the vibrating portion 14, or may be a different ceramic material. As in the case of the vibrating portion 14, ceramic materials constituting the fixing portion include, for example, stabilized zirconium oxide, mullite, aluminum oxide, magnesium oxide, aluminum nitride, silicon nitride, and glass.

The shape of the space is not limited. The horizontal and vertical shapes of the space may be, for example, circular, oval, polygonal including square and rectangular, or a combination thereof. When the shape is polygonal, the corners are preferably rounded.

The detecting portion 20 comprises a piezoelectric film 22, and a first electrode 24 and a second electrode 26 between which the piezoelectric film 22 is held. The first electrode 24 covers at least a part of the outer surface 22s of the piezoelectric film 22, and the second electrode 26 covers at least a part of the surface 14s of the vibrating portion 14.

The piezoelectric film 22 microscopically generates dielectric polarization corresponding to stress, and macroscopically outputs electric signals such as charges and voltages corresponding to stress. It is preferred that the piezoelectric film then undergoes bending displacement in the thickness direction when the vibration portion 14 vibrates. When a particle contacts with the first electrode and/or the vibrating portion, the piezoelectric film 22, together with the vibrating portion 14, vibrates in the thickness direction of the piezoelectric film 22, and this vibration exerts stress to the piezoelectric film 22.

The thickness of the piezoelectric film is preferably 1 to 100 μm, more preferably 5 to 50 μm, and further preferably 5 to 30 μm. If the thickness exceeds 100 μm, sensitivity lowers, and if the thickness is less than 1μm, reliability cannot be obtained.

Although the piezoelectric film preferably comprises a piezoelectric ceramic material, electrostrictive or ferroelectric ceramics may be used, and these materials may or may not require polarization treatment.

Ceramic materials used in the piezoelectric film include, for example, lead zirconate, lead magnesium niobate, lead nickel niobate, lead zinc niobate, lead manganese niobate, lead antimony stannate, lead titanate, lead manganese tungstate, lead cobalt niobate, and barium titanate, or ceramic materials containing the combination of the above compounds. It is needless to say that the ceramic material may be a material which contains 50 percent by weight of these compounds as the main component. Ceramic materials containing lead zirconate is preferably used. To the ceramic materials described above, oxides of lanthanum, calcium, strontium, molybdenum, tungsten, barium, niobium, zinc, nickel, or manganese, the combination of any of these oxides, or other compounds may be added in an adequate amount. It is preferred, for example, that the ceramic material comprises lead magnesium niobate, lead zirconate, and lead titanate as main components, and further contains lanthanum or strontium.

The piezoelectric film may be dense or may be porous. When the film is porous, the void ratio is preferably 40 percent or less.

Also, the piezoelectric film may be of a single layer, or may be of laminated structure of two or more layers. When the film is of laminated structure of two or more layers, these layers may be placed laterally or vertically. Detecting portions may be provided on one side of, or both sides of the vibrating portion.

The first electrode 24 and the second electrode 26 output the electric signals from the piezoelectric film 22 through the lead 28 and the lead 29 to the terminal pads. The second electrode 26, leads 28 and 29, and terminal pads may be formed simultaneously using the thin film method described later.

Although the thickness of the first and second electrodes may be determined depending on uses, the thickness between 0.1 and 50 μm is preferred.

It is preferred that the first electrode is solid at room temperature, and consists of a conductive metal. The conductive metals include, for example, aluminum, titanium, chromium, iron, cobalt, nickel, copper, zinc, niobium, molybdenum, ruthenium, rhodium, silver, tin, tantalum, tungsten, iridium, platinum, gold, and lead, or an alloy thereof. It is needless to say that these chemical elements may be contained in an optional combination. Electrode materials using platinum group metals such as platinum, rhodium, and paradium, or alloys containing platinum group metals such as silver-platinum and platinum-paradium alloys as the main components are preferably used. Copper, silver, and gold are more preferable because of their durability.

It is preferred that the second electrode consists of a high-melting-point metal such as platinum, ruthenium, rhodium, paradium, iridium, titanium, chromium, molybdenum, tantalum, tungsten, nickel, and cobalt, or alloys thereof. Also the second electrode may comprise an optional combination of these high-melting-point metals. Electrode materials using platinum group metals such as platinum, rhodium, and paradium, or alloys containing platinum group metals such as silver-platinum and platinum-paradium alloys as the main components are preferably used. Since the second electrode is often exposed to a high temperature on heat treatment, the metal which resists a hot oxidizing atmosphere is preferable.

Thermet, which contains these high-melting-point metals, and ceramic materials such as alumina, zirconium oxide, silicon oxide, and glass may also be used.

The shape of the substrate is not limited, and is selected depending on uses. Although a plate-like shape is preferred, rod-like or tubular shapes may also be used.

In the following description, the same reference numbers are used for indicating the same articles.

In the embodiments of FIGS. 1 through 3, the detecting portion 20 is located in the inlet 32 side relative to the vibrating portion 14. On the other hand, as FIG. 4 shows, a concave portion 17 may be formed in the substrate 12 so that the vibrating portion 14 becomes thin, and the detecting portion 20 may be located in the outlet 34 side relative to the vibrating portion 14. By this the direct collision of the fluid and particles in the fluid with the detecting portion 20 is prevented, and the durability of the detecting portion 20 is improved. When a concave portion 17 is formed in the substrate 12, the detecting portion 20 may be located in the inlet 32 side relative to the vibrating portion 14.

In the embodiment of FIG. 4, the detecting portion 20 is fixed in the concave portion 17, that is, on the surface 14t of the vibrating portion 14. When a particle in the fluid collides with the surface 14s of the vibrating portion 14, the vibrating portion 14 vibrates vertically, and in turn the detecting portion 20 also vibrates vertically. The detecting portion 20 converts this vibration into electric signals.

In the embodiment of FIG. 4, the concave portion 17 of the substrate 12 is located in the outlet 34 side. While in the embodiment of FIG. 5, the concave portion 17 of the substrate 12 is located in the inlet 32 side, and the detecting portion 20 is located in the outlet 34 side relative to the vibrating portion 14. A part of the fluid flows into the concave portion 17, and solid particles collide with the surface 14t of the vibrating portion 14, and the vibrating portion 14 and the detecting portion 20 vibrate. In the embodiment of FIG. 6, the sensor element of FIG. 4 is deviated from the central axis 46 of the nozzle 33.

Figure 7A:
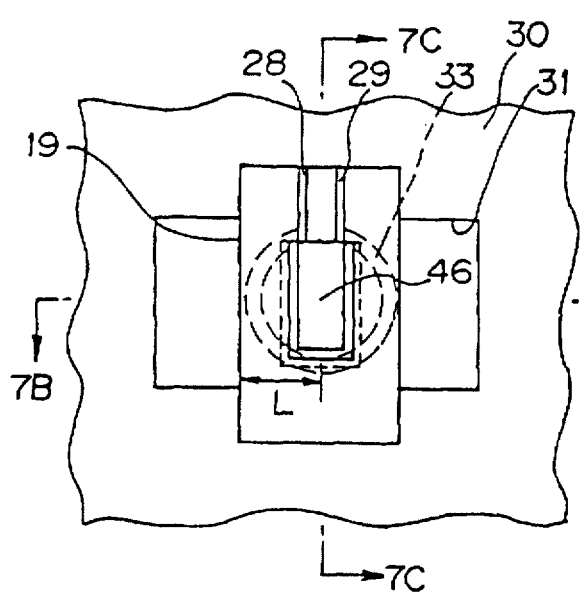
FIGS. 7A, 7B, and 7C are cross-sectional views of an embodiment of the axial-flow particle sensor according to the present invention, FIG. 7A being a front view thereof, FIG. 7B being a cross-sectional view along the line 7C–7C', and FIG. 7C being a cross-sectional view along the line 7B–7B'.
Figure 7B:
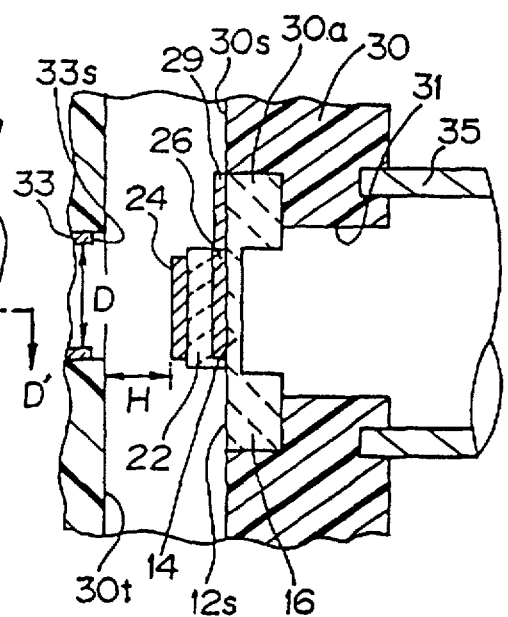
Figure 7C:
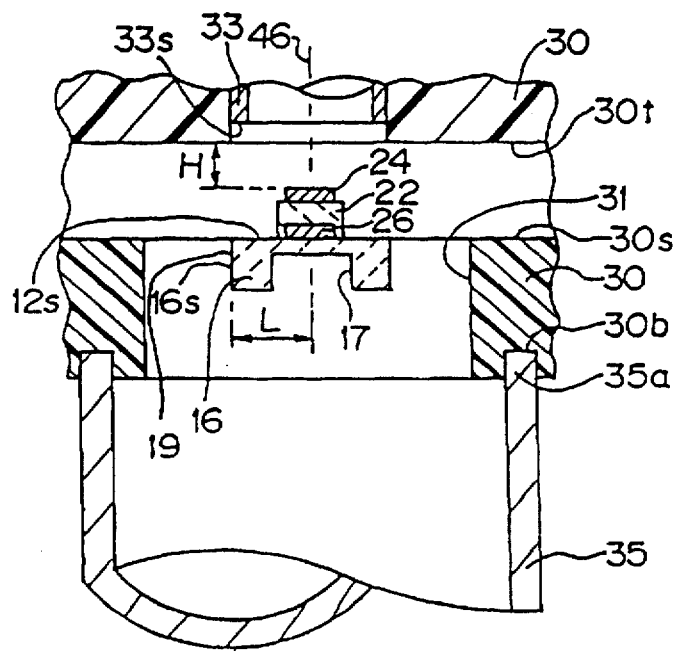

In the embodiment of FIGS. 7A, 7B and 7C, the holes through which the fluid flows are formed as gaps 19 between the ceramic substrate and the housing. An opening 31 is formed on the housing 30, and the plate-like substrate 12 intersects with the opening 31, and is fixed to the housing 30 forming a pair of gaps 19. The gaps 19 are located symmetrically with each other, and have symmetric shapes.

A notch 30a is formed on the housing 30 corresponding to the shape of the fixing portion 16 of the substrate 12, and the fixing portion 16 of the substrate 12 is inserted into the notch 30a. However, the means for fixing the housing 30 with the substrate 12 is not especially limited, and screws or adhesives may be used.

In the embodiment of FIGS. 7A, 7B and 7C, the surface 30s of the housing 30 and the surface 12s of the substrate 12 are formed on the same plane. However, the surface 30s of the housing 30 is not required to be formed on the same plane as the surface 12s of the substrate 12.

The end surface 33s of the nozzle 33 is located inside the inner surface 30t of the housing 30. By this the risk that the sensor element is damaged by the nozzle 33 is minimized. The end surface 35a of the nozzle 35 is inserted and fixed in the concave portion 30b of the housing 30.

Figure 8A:
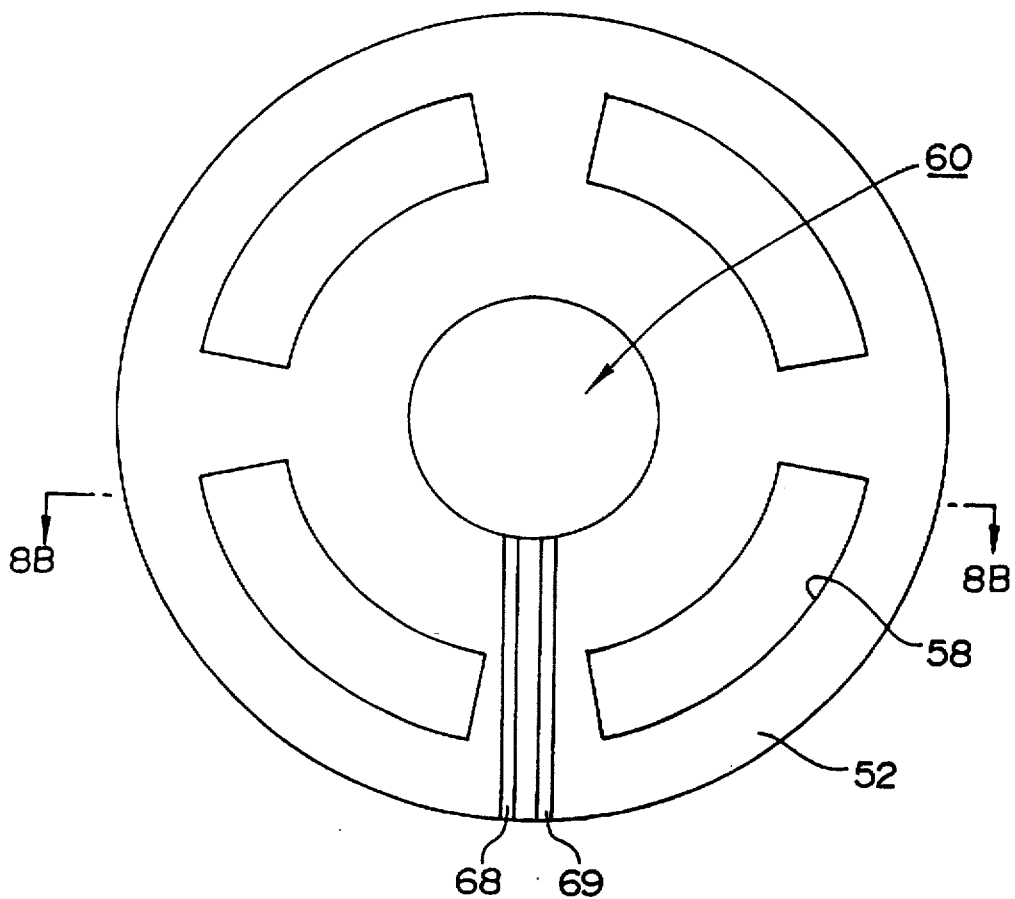
FIGS. 8A and 8B are cross-sectional views of an embodiment of the axial-flow particle sensor according to the present invention, FIG. 8A being a front view thereof, and FIG. 8B being a cross-sectional view along the line 8B–8B'.
Figure 8B:
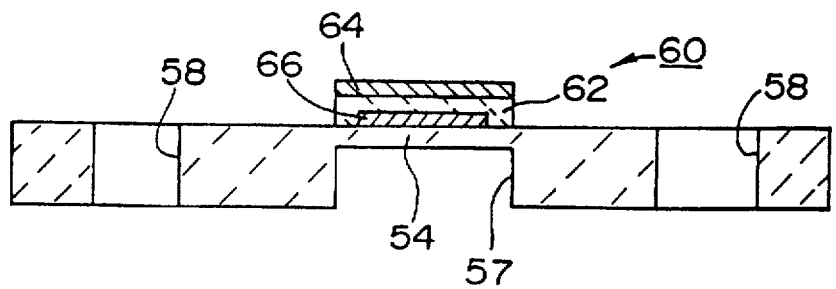

In the embodiment of FIGS. 8A and 8B, four fan-shaped throughholes 58 are formed in the disc-shaped substrate 52. A fan-shaped throughhole has a pair of arcs, which are preferably concentric with the substrate 52. A concave portion 57 is formed at the center of the substrate 52 concentrically with of substrate 52 for forming the vibrating portion 54.

On the surface 54s of the disc-shaped vibrating portion 54, a disc-shaped detecting portion 60 is fixed concentrically with the substrate 52. The detecting portion 60 has a piezoelectric film 62, and a first electrode 64 and a second electrode 66 between which the piezoelectric film 62 is fixed. The first electrode 64 is connected to a lead 68, and the second electrode 66 is connected to a lead 69.

It is not required that the number of throughholes is 4, but any number such as 2, 3, 5, 6, and 7 may be used. When the substrate is disc-shaped, the throughholes are preferably fan-shaped having arcs concentric with the substrate. By this the flow of the fluid may be controlled symmetrically. However, the shape of the throughholes is not specifically limited.

A method for producing the sensor element 10 will be described below.

The substrate is integrated by laminating forming layers which are green sheets or green tapes by a method such as hot pressing, then sintering. For example, in the substrate 12 of FIG. 1, three layers of green sheets or green tapes are laminated, and a hole of a desired shape to become a closed space 15 is formed in the second layer before laminating. The layers may also be formed by compression molding, casting, or injection molding, and the space may be provided by cutting, machining, laser processing, or pressing. Although it is not required that the layers have the same thickness, it is preferred that the layers undergo the similar shrinkage due to sintering.

The green sheets or green tapes before sintering may be formed to have a shape corresponding to the concave portion, and the concave portion may be formed by machining after sintering.

A method for forming the detecting portion 20 on the ceramic vibrating portion 14 will next be described. A piezoelectric body is formed by pressing using a mold or by tape forming using a slurry material, and this piezoelectric body before sintering is laminated on the vibrating portion of the substrate before sintering by hot pressing, and simultaneously sintered to form the substrate and the piezoelectric body. In this case, the electrodes must be formed on the substrate or the piezoelectric body beforehand by the film forming method described later.

Although the sintering temperature for the piezoelectric film is determined depending on the constituting materials, the sintering temperature is generally 800° to 1400° C., preferably 1000° to 1400° C. In this case, it is preferred for controlling the composition of the piezoelectric film to conduct sintering in the presence of the evaporation source of the components of the piezoelectric film.

In the film forming method, on the other hand, the second electrode 26, the piezoelectric film 22, and the first electrode 24 are laminated in this order on the vibration portion 14 to form the detecting portion 20. Although film forming methods well-known in the art may be used, for example, thick film methods such as screen printing, coating methods such as dipping, and thin film methods such as ion beam, spattering, vacuum deposition, ion plating, chemical vapor deposition (CVD), and electroplating methods may be used, the method is not limited to these methods. Among these methods, screen printing is preferred because of stable production. The second electrode 26, leads 28 and 29, and terminal pads can be simultaneously applied by screen printing. The piezoelectric film 22 is preferably formed by screen printing, dipping, and painting. In these methods, the film can be formed on the substrate using paste or slurry containing ceramic particles consisting of the materials for the piezoelectric film as the main component, and good properties for the piezoelectric body are obtained. When the piezoelectric film is formed by the film forming method, since the detecting portion and the vibrating portion can be joined integrally without using adhesives, this method is especially preferred because of high reliability and reproducibility, and the ease of integration. Such a film may have suitable patterns. These patterns may be formed by screen printing or photolithography, or may be formed by removing unnecessary portions using a mechanical processing such as laser processing, slicing, and ultrasonic processing.

The shapes of the piezoelectric film and the first and second electrodes are not limited, and any shape may be used depending on the use. For example, the shape may be polygonal such as triangular and rectangular, curved shapes such as circular, oval, and annular, comb-shaped, lattice-shaped, or a combination of these shapes. It is not required to provide the detecting portion 20 on the entire surface of the vibrating portion 14, but it is preferred to provide it on the part where strain due to vibration is largest.

Each film (22, 24, and 26) thus formed on the substrate may be integral with the substrate by heat treatment each time the film is formed, or may be joined integrally with the substrate by heat-treating these films at the same time after forming these films. When the first and second electrodes are formed by the thin film method, heat treatment is not always necessary for integrating these electrodes.

Throughholes 18 may be formed in the layers obtained using green sheets or green tapes, or using a mold at the same time as the substrate is formed, by mechanical processing such as cutting, grinding, or punching by pressing. That is, green sheets and the like may be machined corresponding to the shape of the throughholes. Throughholes may be formed by mechanical processing such as laser processing, cutting, and ultrasonic processing after sintering the substrate. Also, the throughholes may be formed after forming the detecting portion using the same processing methods. Furthermore, throughholes may be formed after forming and sintering a concave portion or a closed space corresponding to the shape of the throughholes using green sheets and green tapes by mechanical processing.

When a particle collides with the detecting portion 20 or the vibrating portion 14, a voltage pulse is generated. This voltage pulse generally has a wave form similar to the wave known as the attenuating sine wave. The amplitude of the attenuating sine wave is proportional to the size and the velocity of the particles. When the flow rate of the fluid is relatively stable, and the velocity of the particles is deemed to be almost constant, the amplitude of the attenuating sine wave reflects adequately the size of the particle which collides with the vibrating portion. Therefore, by using an appropriate electric circuit, the amplitude of the attenuating sine wave can be obtained, and the distribution of the particle diameters can be obtained directly from the distribution of the amplitudes of the attenuating sine wave.

The output signals from the detecting portion are preferably amplified by an amplifier circuit, and amplified signals are input to a central processor and the like.

When the axial flow particle sensor of the present invention is used for detecting particles contained in a lubricant for car engines, the axial flow particle sensor may be installed in the oil line of the engine. The axial flow particle sensor may also be installed in the bypass provided on the oil line.

The present invention has been described above mainly using a piezoelectric film which utilize piezoelectricity as the device for detecting the vibration of the vibrating portion and converting the vibration into electric signals. However, the above converter is not limited to the device utilizing piezoelectricity.

For example, the device utilizing electromagnetic induction comprises a coil provided on the vibrating portion, an electric circuit for detecting electric signals flowing in this coil, and a magnet (which may be an electromagnet) forming a magnetic field in the coil. When the coil vibrates together with the vibrating portion, a current flows in the coil due to electromagnetic induction, and is detected by the electric circuit.

The device utilizing change in static capacity comprises a pair of electrodes installed on the surface of the vibrating portion, a dielectric held between these electrodes, and an electric circuit connected to the electrodes, and static capacity charged in this specific space is detected by the electric circuit.

An apparatus for irradiating the vibrating portion and for utilizing change in incident light at the receiving portion has a device for irradiating the vibrating portion such as a photodiode, and a device for measuring the amount of light reflected by the vibrating portion. The device for measuring the amount of light reflected by the vibrating portion includes a photosensor. As the vibrating portion vibrates, the amount of light reflected by the vibrating portion changes, and change in the amount of light is measured.

An apparatus utilizing change in electric resistance for the strain of the conductor has a conductor installed on the surface of the vibrating portion, and an electric circuit connected to this conductor. When the conductor vibrates together with the vibrating portion, since the conductor is strained by vibration and resistance changes, change in resistance is detected by the electric circuit.

An apparatus utilizing change in electric resistance for the strain of the semiconductor has a semiconductor installed on the surface of the vibrating portion, and an electric circuit connected to this semiconductor. When the semiconductor vibrates together with the vibrating portion, since the semiconductor is strained by vibration and resistance changes, change in resistance is detected by the electric circuit.

According to the axial flow particle sensor of the present invention, the probability that the flow of the fluid collides with the vibrating portion or the detecting portion increases, and detecting sensitivity is improved by controlling the flow of a fluid in the vicinity of the sensor element. Especially, sensitivity of detecting fine particles of a particle diameter of 10 µm or less is improved.

The present invention has been described based on several embodiments, these embodiments should not be translated as the limitation of the present invention, but may be altered, changed, or improved within the scope of the present invention based on the knowledge of those skilled in the art.

What is claimed is:

1. An axial-flow particle sensor comprising:
    a sensor element comprising a vibrating portion having a sufficient mass for responding to the collision of a solid particle in a fluid and a converter for detecting the vibration of said vibrating portion and converting the vibration to electric signals;
    a housing for fixing said sensor element;
    an inlet of fluid; and
    an outlet of fluid;
    wherein said outlet is located in the opposite side of said inlet relative to said sensor element, a throughhole is opened in at least a part of the circumference of said vibrating portion, and said vibrating portion of said sensor element is located at the extension of fluid flow formed at said inlet so that the fluid entering from said inlet flows through said throughhole and flows out from said outlet.

2. An axial-flow particle sensor according to claim 1 wherein said inlet is placed coaxially with said outlet, and said vibrating portion of said sensor element is placed coaxially with said inlet and said outlet.

3. An axial-flow particle sensor according to claim 2 wherein said vibrating portion has a plate-like form, and the extending direction of the plate of said vibrating portion is almost perpendicular to the direction of fluid flow formed at said inlet.

4. An axial-flow particle sensor according to claim 1 wherein two or more throughholes are formed symmetrically with said axis.

5. An axial-flow particle sensor according to claim 1 wherein said sensor element comprises a ceramic substrate, said vibrating portion is a part of said ceramic substrate, and said throughhole is formed through said ceramic substrate.

6. An axial-flow particle sensor according to claim 1 wherein said sensor element comprises a ceramic substrate, said vibrating portion is a part of said ceramic substrate, and said throughhole is a gap between said ceramic substrate and said housing.

7. An axial-flow particle sensor according to claim 1 wherein said converter is disposed on said inlet side relative to said vibrating portion.

8. An axial-flow particle sensor according to claim 1 wherein said converter is disposed on said outlet side relative to said vibrating portion.

9. An axial-flow particle sensor according to claim 1 wherein the sectional area of said inlet is smaller than the sectional area of said outlet.

10. An axial-flow particle sensor according to claim 1 wherein said converter is one selected from the group consisting of:

that utilizing piezoelectricity, that utilizing electromagnetic induction, that utilizing change in static capacitance, that emitting light on to said vibration portion and utilizing change in incident light at the light receiving portion, that utilizing change in electric resistance due to the strain of the conductor, and that utilizing change in electric resistance due to the strain of the semiconductor, or a combination thereof.

11. An axial-flow particle sensor according to claim 1 wherein said sensor element comprises:

a detecting portion having a piezoelectric film consisting of a ceramic material, a first electrode covering at least a part of the outer surface of said piezoelectric film, and a second electrode covering at least a part of the inner surface of said piezoelectric film, a vibrating portion carrying said detecting portion and consisting of a ceramic material, and a fixing portion for fixing said vibrating portion so as to allow said vibrating portion to vibrate.

* * * * *